(12) United States Patent
Fadhel et al.

(10) Patent No.: US 10,522,765 B2
(45) Date of Patent: Dec. 31, 2019

(54) ORGANIC ELECTRONIC DEVICE HAVING LITHOXY GROUP AND PHOSPHINE OXIDE GROUP MATERIAL

(71) Applicants: Novaled GmbH, Dresden (DE); University of Rennes, Rennes (FR)

(72) Inventors: Omrane Fadhel, Dresden (DE); Julien Frey, Dresden (DE); Wylliam Delaunay, Rennes (FR); Muriel Hissler, Rennes (FR)

(73) Assignees: Novaled GmbH, Dresden (DE); University of Rennes, Rennes (FR)

( * ) Notice: Subject to any disclaimer, the term of this patent is extended or adjusted under 35 U.S.C. 154(b) by 107 days.

(21) Appl. No.: 15/515,751

(22) PCT Filed: Sep. 29, 2015

(86) PCT No.: PCT/EP2015/072384
§ 371 (c)(1),
(2) Date: Mar. 30, 2017

(87) PCT Pub. No.: WO2016/050748
PCT Pub. Date: Apr. 7, 2016

(65) Prior Publication Data
US 2018/0331300 A1 Nov. 15, 2018

(30) Foreign Application Priority Data
Sep. 30, 2014 (EP) ..................................... 14186957

(51) Int. Cl.
*H01L 29/08* (2006.01)
*H01L 33/00* (2010.01)
(Continued)

(52) U.S. Cl.
CPC ...... *H01L 51/0071* (2013.01); *C07F 9/65685* (2013.01); *H01L 51/0562* (2013.01);
(Continued)

(58) Field of Classification Search
CPC .................. H01L 51/0071; C07F 9/65685
See application file for complete search history.

(56) References Cited

U.S. PATENT DOCUMENTS 10,297,767 B2    5/2019  Dorok et al.
10,374,165 B2 *  8/2019  Dorok ................... C07F 9/5325
2014/0034932 A1  2/2014  Seo et al.

FOREIGN PATENT DOCUMENTS

EP    2811000 A1    12/2014
JP    2007088015 A   4/2007
(Continued)

OTHER PUBLICATIONS

European Search Report for EP Application No. 14 18 6957 dated Apr. 13, 2015 (6 pages).
(Continued)

*Primary Examiner* — Alonzo Chambliss
(74) *Attorney, Agent, or Firm* — Eversheds Sutherland (US) LLP

(57) ABSTRACT

The present invention relates to an organic electronic device, comprising a first electrode (11), a second electrode (14), and, between the first and the second electrode, a substantially organic layer (13) comprising a heterocyclic compound bearing at least one lithoxy group and containing at least one heterocyclic ring comprising a phosphine oxide group directly bound to three carbon atoms; a compound for use in such an organic electronic device and to a semiconducting material comprising the respective compound.

16 Claims, 1 Drawing Sheet

(51) Int. Cl.
  *H01L 31/0232*  (2014.01)
  *H01L 21/00*    (2006.01)
  *H01L 51/40*    (2006.01)
  *H01L 51/00*    (2006.01)
  *C07F 9/6568*   (2006.01)
  *H01L 51/50*    (2006.01)
  *H01L 51/05*    (2006.01)
  *H01L 51/42*    (2006.01)

(52) U.S. Cl.
  CPC ........ *H01L 51/424* (2013.01); *H01L 51/5076* (2013.01); *H01L 51/5092* (2013.01)

(56) References Cited

FOREIGN PATENT DOCUMENTS

| WO | 2013/079676 A1 | 6/2013 |
| WO | 2013/079678 A1 | 6/2013 |
| WO | 2016/050748 A3 | 4/2016 |

OTHER PUBLICATIONS

PCT International Search Report and Written Opinion for PCT Application No. PCT/EP2015/072384 dated Apr. 6, 2016 (14 pages).
Aleksanyan et al., "Lithium, Zinc and Scandium Complexes of Phosphorylated Salicyladimines: Synthesis, Structure, Thermochemical and Photophysical Properties, and Application in OLEDs," The Royal Society of Chemistry, 2013, 3:24484-24491.
Chinese Office Action for CN Application No. 201580053180.2 dated Aug. 30, 2019 (12 pages with English translation).

\* cited by examiner

ORGANIC ELECTRONIC DEVICE HAVING LITHOXY GROUP AND PHOSPHINE OXIDE GROUP MATERIAL

CROSS REFERENCE TO RELATED APPLICATIONS

This application is a U.S. national stage application of PCT/EP2015/072384, filed Sep. 29, 2015, which claims priority to European Application No. 14186957.8, filed Sep. 30, 2014. The contents of these applications are hereby incorporated by reference.

The present invention relates to an organic electronic device, to a specific compound for use in such an organic electronic device and to a semiconducting material comprising the inventive compound.

Organic semiconductors can be used to fabricate simple electronic components, e.g. resistors, diodes, field effect transistors, and also optoelectronic components like organic light emitting devices, e.g. organic light emitting diodes (OLED). The industrial and economic significance of the organic semiconductors and devices using them is reflected in the increasing industry focus on the subject.

OLEDs are based on the principle of electroluminescence in which electron-hole pairs, so-called excitons, recombine under the emission of light. To this end the OLED is constructed in the form of a sandwich structure wherein at least one organic film is arranged as active material between two electrodes, positive and negative charge carriers are injected into the organic material by an external voltage applied on the electrodes, and the subsequent charge transport brings holes and electrons to a recombination zone in the organic layer (emitting layer, EML), where a recombination of the oppositely charged charge carriers to singlet and/or triplet excitons occurs.

The subsequent radiative recombination of excitons causes the emission of the visible useful light. In order that this light can leave the component, at least one of the electrodes must be transparent. Typically, a transparent electrode consists of conductive oxides designated as TCOs (transparent conductive oxides). Alternatively, a very thin metal electrode can be used. The starting point in the manufacture of an OLED is a substrate on which the individual layers of the OLED are applied. If the electrode nearest to the substrate is transparent, the component is designated as a "bottom-emitting OLED". If the other electrode is designed to be transparent, the component is designated as a "top-emitting OLED". The layers of the OLEDs can comprise small molecules, polymers, or be hybrid.

Operational parameters of OLEDs are being constantly improved to enhance the overall power efficiency. One important parameter is the operation voltage which can be tuned by improving the transport of charge carriers and/or reducing energy barriers such as the injection barriers from the electrodes. Another important figure is the quantum efficiency, and also very relevant is the lifetime of the device. Other organic devices, such as organic solar cells also require improving in efficiency, which nowadays, are at best at about 10%.

Like an OLED, an organic solar cell has a stack of organic layers between two electrodes. In a solar cell, there must be at least one organic layer responsible for the absorption of light and a interface which separates the excitons created by the absorption (photo-active). The interface can be a bi-layer heterojunction, a bulk-heterojunction, or can comprise more layers, e.g., in a step wise interface. Also sensitizing layers and others can be provided. For increased efficiency, a good charge carrier transport is required, in some device structures the transport regions must not absorb light, therefore transport layers and photo-active layers may comprise different materials. Also charge carrier and/or exciton blocking layers may be employed. Highest efficiency solar-cells are, nowadays, multi-layer solar cells, some device structures are stacked (multi-junction solar cells) and connected by a connecting unit (also called recombination layer); nevertheless, single junction solar cells could have a high performance if the right materials were found. Examples of solar devices are given in US2009217980, or in US2009235971.

Differently than OLEDs and organic solar cells, transistors do not require doping of the entire semiconducting (channel) layer, because the concentration of available charge carriers is determined by an electric field supplied by a third electrode (gate electrode). However, conventional organic thin film transistors (OTFTs) require very high voltages to operate. There is a need to lower this operating voltage; such optimization can be done, e.g., with appropriate injection layers.

Organic transistors are also called organic field-effect transistors (OFETs). It is anticipated that a large number of OTFTs can be used for example in inexpensive integrated circuits for non-contact identification tags (RFID) but also for screen control. In order to achieve inexpensive applications, generally thin-layer processes are required to manufacture the transistors. In recent years, performance features have been improved to such an extent that the commercialization of organic transistors is foreseeable. For example, high field-effect mobilities of up to 5.5 $cm^2/Vs$ for holes have been reported in OTFTs utilizing pentacene (Lee et al., Appl. Lett. 88, 162109 (2006)). A typical organic field-effect transistor comprises an active layer of organic semiconducting material (semiconducting layer) which during the operation forms an electrical conduction channel, a drain electrode and a source electrode which exchange electrical charges with the semiconducting layer, and a gate electrode which is electrically insulated from the semiconducting layer by a dielectric layer.

There is a clear need to improve charge carrier injection and/or conductivity in organic electronic devices. Reducing or eliminating the barrier for charge injection between the electrode and the electron transport material (ETM) contributes strongly to enhancement of the device efficiency. Nowadays, there are two main approaches to reduce voltage and enhance efficiencies of organic electronic devices: improvement of the charge carrier injection and improvement of the conductivity of the transport layers. Both approaches can be used in combination.

For instance, U.S. Pat. No. 7,074,500 discloses a component structure for an OLED which leads to a greatly improved charge carrier injection from the electrodes into the organic layers. This effect is based on considerable band bending of the energy levels in the organic layer at the interface to the electrodes, as a result of which injection of charge carriers on the basis of a tunnel mechanism is possible. The high conductivity of the doped layers also decreases the voltage drop which occurs there during operation of the OLED. The injection barriers which may occur in OLEDs between the electrodes and the charge carrier transport layers are one of the main causes for an increase in the operating voltage compared to the thermodynamically justified minimum operating voltages. For this reason, many attempts have been made to reduce the injection barriers, for example by using cathode materials with a low work function, for example metals such as calcium or barium. However, these materials are highly reactive, difficult to process and are only suitable to a limited extent as electrode materials. Moreover, any reduction in operating voltage brought about by using such cathodes is only partial.

Metals having low work function, in particular alkali metals such as Li and Cs, are often used either as the cathode material or the injection layer to promote electron injection. They have also widely been used as electrical dopants in order to increase the conductivity of the ETM, see e.g. U.S. Pat. Nos. 6,013,384, 6,589,673. Metals like Li or Cs provide a high conductivity in matrixes which are difficult to dope otherwise (e.g. BPhen, Alq3).

However, the use of low work function metals has several disadvantages. It is well known that the metals can easily diffuse through the semiconductor, eventually arriving at the optically active layer and quenching the excitons, thereby lowering the efficiency of the device and the lifetime. Another disadvantage is their high susceptibility to oxidation upon exposure to air. Therefore, devices using such metals as dopants, injection or cathode material require rigorous exclusion of air during production and rigorous encapsulation afterwards. Another well-known disadvantage is that higher doping concentration of the dopant exceeding 10 mol. % may increase the undesired absorption of light in the doped charge transport layers. Yet another problem is high volatility of many simple redox dopants like Cs, leading to cross-contamination in the device assembling process making their use in device fabrication tools difficult.

Another approach to replace metals as n-dopants and/or injection materials for ETM is the use of compounds with strong donor properties, such as tetrakis(1,3,4,6,7,8-hexahydro-2H-pyrimido[1,2-a]pyrimidinato)ditungsten (II) ($W_2$(hpp)$_4$) or Co(Cp*)$_2$ (US2009/0212280, WO2003/088271) which have similar or slightly less doping/injecting ability in comparison with alkaline earth metals. These compounds have more favourably lower volatilities than alkali metals and their diffusion through the doped layers is strongly impeded by their high molar mass, however, due to their still high electron donating capability, they are still undergoing rapid decay upon exposure to air, what makes their handling in device production difficult too.

Another alternative approach consists in mixing metal organic complexes such as lithium quinolate (LiQ) into an electron transport layer. The exact mechanism of the voltage improvement is not yet sufficiently clarified. Devices using LiQ as electrical dopant for improving voltage still show significantly higher operating voltages in comparison with devices doped with strongly reductive metals or with strongly reductive organic redox dopants.

Therefore, it is very desirable to provide materials which possess high doping/charge injection capability, allowing for highly efficient organic electronic devices, substantially preserving the long-term stability of the device and which are infinitely stable in air.

It is therefore an objective of the present invention to provide an organic electronic device, which overcomes state of the art limitations mentioned above and have improved performance compared to electronic devices of the prior art in terms of reduced operating voltage and higher power efficiency. Another object of the invention is a compound enabling the organic electronic devices with improved performance. A third object of the invention is a semiconducting material comprising the inventive compound.

SUMMARY OF THE INVENTION

The first object is achieved by an organic electronic device, comprising a first electrode, a second electrode, and, between the first and the second electrode, a substantially organic layer comprising a heterocyclic compound bearing at least one lithoxy group and containing at least one heterocyclic ring comprising a phosphine oxide group directly bound to three carbon atoms.

Lithoxy group is to be understood as a hydroxy group having its hydrogen replaced with lithium. It is to be understood that the bond between oxygen and lithium is a very polar bond having in a great extent ionic character. Nevertheless, as any chemical bond has also certain covalent character, the lithoxy group can be also described in terms of formulae used in organic chemistry, wherein a sigma covalent bond is described by means of a single line between two atoms.

Preferably, the lithoxy group is directly attached to an aromatic or heteroaromatic structural moiety. Also preferably, the heterocyclic ring comprising the phosphine oxide group is a five-, six- or seven-membered ring.

More preferably, the heterocyclic compound comprised in the substantially organic layer is a compound according to formula (I):

formula (I)

wherein $A^1$ is a $C_6$-$C_{30}$ arylene or $C_2$-$C_{30}$ heteroarylene, each of $A^2$ and $A^3$ is independently selected from a $C_6$-$C_{30}$ aryl and $C_2$-$C_{30}$ heteroaryl, and $A^2$ with $A^3$ are linked to each other.

The aryl, heteroaryl, arylene or heteroarylene may be unsubstituted or substituted with groups comprising C and H or with a further LiO group. It is supposed that the given C count in an aryl, heteroaryl, arylene or arylene group includes also all substituents present on the said group.

It is to be understood that the term substituted or unsubstituted arylene or heteroarylene stands for a divalent radical derived from substituted or unsubstituted arene or heteroarene, wherein the both structural moieties adjacent in formula (I) to $A^1$ (the OLi group and the PO$A^2A^3$ group) are attached directly to an aromatic ring of the arylene or heteroarylene group. Examples of simple arylenes are o-, m- and p-phenylene. If $A^1$ is a polydyclic arylene, the groups OLi and PO$A^2A^3$ may be either both attached to the same ring of the polycyclic arylene, or each of them may be attached to different rings of the polycyclic arylene.

In case of (hetero)arylenes derived from the polycyclic (hetero)arenes, the definition of o-, m- and p-substitution is generalized as follows. (Hetero)arylenes, wherein OLi and PO$A^2A^3$ are attached to two neighbour carbon atoms that are directly attached to each other in the same aromatic ring, are understood as o-(hetero)arylenes. All (hetero)arylenes having the substituents OLi and PO$A^2A^3$ attached to the opposite sides of a rigid arene structure so that the bonds to these substituents are parallel, are defined as p-(hetero)arylenes, whereas in m-(hetero)arylenes, there is at least one atom between the C atoms to which OLi and PO$A^2A^3$ are attached and the angle between the bonds attaching the OLi and the PO$A^2A^3$ moieties is different from 180° (in the rigid aromatic structures) or variable, e.g. in (hetero)arylenes consisting of two or more rigid (hetero)arylene substructures bound together by single bonds.

Examples of generalized p-(hetero)arylenes are naphthalene-1,4-diyl, naphthalene-1,5-diyl, naphthalene-2,6-diyl, 1,1'-biphenyl-4,4'-diyl, pyridine-2,5-diyl, quinoline-2,6-diyl, quinoline-3,7-diyl, quinoline-4,8-diyl, quinoline-5,8-diyl. Examples of generalized m-(hetero)arylenes are naphthalene-1,3-diyl, naphthalene-1,6-diyl, naphthalene-1,7-diyl, naphthalene-1,8-diyl, naphthalene-2,7-diyl, 1,1'-biphenyl-3,4'-diyl, 1,1'-biphenyl-2,4'-diyl, 1,1'-biphenyl-2,4'-diyl, 1,1'-biphenyl-2,3'-diyl, 1,1'-biphenyl-3,3'-diyl, 1,1'-biphenyl-2,2'-diyl, pyridine-2,6-diyl, pyridine-2,4-diyl, pyridine-3,5-diyl, quinoline-2,8-diyl, thiophene-2,4-diyl, thiophene-2,5-diyl, furan-2,4-diyl, furan-2,5-diyl.

Preferably, $A^1$ is $C_6$-$C_{12}$ arylene or $C_2$-$C_{12}$ heteroarylene. Even preferably, each of $A^2$-$A^3$ is independently selected from a $C_6$-$C_{10}$ aryl or $C_2$-$C_{12}$ heteroaryl. More preferably, both $A^2$ and $A^3$ are independently selected from phenyl and pyridyl. Most preferably, $A^1$ is phenylene or pyridine-diyl.

In one preferred embodiment, the substantially organic layer comprises an electron transport matrix compound.

In a further preferred embodiment, the electron transport matrix comprises an imidazole or a P=O functional group.

Moreover, the heterocyclic compound bearing at least one lithoxy group and containing at least one heterocyclic ring comprising a phosphine oxide group directly bound to three carbon atoms (preferably a compound according to formula (I)) and the electron transport matrix compound are preferably present in the substantially organic layer in the form of a homogeneous mixture.

Furthermore, the organic electronic device may be selected from an organic light emitting diode, organic solar cell and organic field effect transistor.

Preferred is an organic electronic device wherein the device is an organic light emitting diode with the first electrode being an anode, the second electrode being a cathode, and the device further comprising a light emitting layer (EML) between the anode and the cathode and wherein the substantially organic layer is comprised between the cathode and the EML.

Alternatively or in addition, the EML of the organic electronic device comprises a light emitting polymer.

The second object of the present invention is achieved by compound according to formula (I)

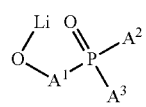

formula (I)

wherein $A^1$ is a $C_6$-$C_{30}$ arylene or $C_2$-$C_{30}$ heteroarylene, each of $A^2$ and $A^3$ is independently selected from a $C_6$-$C_{30}$ aryl and $C_2$-$C_{30}$ heteroaryl, and $A^2$ with $A^3$ are linked to each other.

The aryl, heteroaryl, arylene or heteroarylene may be unsubstituted or substituted with groups comprising C and H or with a further LiO group. It is supposed that the given C count in an aryl, heteroaryl, arylene or arylene group includes also all substituents present on the said group.

Preferably, $A^1$ is $C_6$-$C_{12}$ arylene or $C_2$-$C_{12}$ heteroarylene. Even preferably, each of $A^2$-$A^3$ is independently selected from a $C_6$-$C_{10}$ aryl or $C_2$-$C_{12}$ heteroaryl. More preferably, both $A^2$ and $A^3$ are independently selected from phenyl and pyridyl. Most preferably, $A^1$ is phenylene or pyridine-diyl.

In one of preferred embodiments, $A^1$, $A^2$ and $A^3$ are o-phenylene.

Preferred use of the heterocyclic compound bearing at least one lithoxy group and containing at least one heterocyclic ring comprising a phosphine oxide group directly bound to three carbon atoms (preferably of the compound according to formula (I)) in an organic electronic device is as an electrical dopant in an electron transport layer of the device and/or in a layer adjacent to the electron transport layer.

The third object of the present invention is achieved by an electrically doped semiconducting material comprising at least one electron transport matrix compound and at least one heterocyclic compound bearing at least one lithoxy group and containing at least one heterocyclic ring comprising a phosphine oxide group directly bound to three carbon atoms (preferably compound according to formula (I)).

The object of the invention is further achieved by compound having formula (Ia)

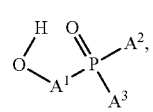

formula (Ia)

wherein $A^1$ is a $C_6$-$C_{30}$ arylene or $C_2$-$C_{30}$ heteroarylene, each of $A^2$ and $A^3$ is independently selected from a $C_6$-$C_{30}$ aryl and $C_2$-$C_{30}$ heteroaryl, and $A^2$ with $A^3$ are linked to each other, as a penultimate precursor for compound having formula (I).

DETAILED DESCRIPTION OF THE INVENTION

Preferably, the heterocyclic compound bearing at least one lithoxy group and containing at least one heterocyclic ring comprising a phosphine oxide group directly bound to three carbon atoms (also preferably, compound according to formula (I)) is used in transport and/or injection layers, more preferably in an electron transport layer and/or electron injection layer, most preferably in the form of the electrically doped semiconducting material according to the invention.

Heterocyclic compounds bearing at least one lithoxy group and containing at least one heterocyclic ring comprising a phosphine oxide group directly bound to three carbon atoms (preferably compounds according to formula (I)) are air-stable and capable to be evaporated without decomposition. They are also soluble in a variety of solvents. This makes the compounds according to formula (I) particularly easy to use in manufacturing processes.

The inventive organic electronic device preferably comprises a layered structure including a substrate, an anode and a cathode, the at least one substantially organic layer being disposed within the layered structure between the anode and the cathode.

The substantially organic layer may further comprise an electron transport matrix compound.

Preferably, the electron transport matrix compound and the compound bearing at least one lithoxy group and containing at least one heterocyclic ring comprising a phosphine oxide group directly bound to three carbon atoms (preferably, a compound according to formula (I)) form a homogeneous mixture. The compound bearing at least one lithoxy group and containing at least one heterocyclic ring comprising a phosphine oxide group directly bound to three carbon atoms (preferably, compound (I)) constitutes preferably 10 weight % or more of the substantially organic layer. More preferred is 40 wt. % or more. For an electron transport layer, it is however preferred that the electron transport matrix is the main component of the layer.

As matrix materials for electron transport layers, use may be made for example of fullerenes, such as for example $C_{60}$, oxadiazole derivatives, such as for example 2-(4-biphenyl)-5-(4-tert-butylphenyl)-1,3,4-oxadiazole, quinoline-based compounds such as for example bis(phenylquinoxalines), or oligothiophenes, perylene derivatives, such as e.g. perylenetetracarboxylic acid dianhydride, naphthalene derivatives such as e.g. naphthalenetetracarboxylic acid dianhydride, or other similar compounds known as matrices in electron transport materials.

It is preferred that the electron transport material comprises a phosphine oxide or imidazole functional groups.

Compounds well suitable as electron transport materials are compounds from:

US2007/0138950, preferentially, compounds (1) and (2) on page 22, compounds (3), (4), (5), (6), and (7) on page 23, compounds (8), (9), and (10) on page 25, and compounds (11), (12), (13), and (14) on page 26, which compounds are incorporated herein by reference;

US2009/0278115 A1, preferentially, compounds (1) and (2) on page 18, which compounds are incorporated herein by reference;

compounds from US2007/0018154, preferentially the compounds of claim 10, formula 1-1, 1-2, 1-3, 1-4, 1-5, 1-6 on page 19, 1-7 to 1-146 on pages 20 to 26. Compounds from US2008/0284325 A[1], preferentially compounds on page 4: 2-(4-(9,10-diphenylanthracen-2-yl)phenyl)-1-phenyl-1H-benzo[d]imidazole, 2-(4-(9,10-di([1,1'-biphenyl]-2-yl) anthracen-2-yl)phenyl)-1-phenyl-1H-benzo[d]imidazole, 2-(4-(9,10-di(naphthalen-1-yl) anthracen-2-yl) phenyl)-1-phenyl-1H-benzo[d]imidazole, 2-(4-(9,10-di(naphthalen-2-yl) anthracen-2-yl) phenyl)-1-phenyl-1H-benzo[d]imidazole, 2-(4-(9,10-di([1, 1':3',1"-terphenyl]-5'-yl) anthracen-2-yl)phenyl)-1-phenyl-1H-benzo[d]imidazole, and the compound on page 5, which compounds are incorporated herein by reference;

naphthacene derivatives from US2007/0222373, preferentially, compounds (A-1) and (A-2) from page 17, compounds (A-3) from page 18 and (A-4) from page 19, which compounds are incorporated herein by reference;

compounds from US2008/0111473, preferentially, compound 1 on page 61, compound 2 on page 62, compounds 3 and 4 on page 63, compound 5 on page 64, and compound 6 on page 65, which compounds are incorporated herein by reference;

compound H-4 from page 20, and compounds (1) and (2) of page 12 of US2010/0157131, which compounds are incorporated herein by reference;

compounds from US2010/0123390, according to general formula (1), preferentially, compounds H4, H5 p. 21, H7 p. 22, H11, H12, H13 p. 23, H16, and H18 p. 24, which compounds are incorporated herein by reference;

US2007/0267970, preferentially 2-([1,1'-biphenyl]-4-yl)-1-(4-(10-(naphthalen-2-yl) anthracen-9-yl)phenyl)-2,7a-dihydro-1H-benzo[d]imidazole (compound 1), 2-([1,1'-biphenyl]-2-yl)-1-(4-(10-(naphthalen-2-yl)anthracen-9-yl)phenyl)-2,7a-dihydro-1H-benzo[d]imidazole (compound 2). Compound (C-1) from US2007/0196688, p. 18, which is incorporated herein by reference;

Other suitable compounds are 7-(4'-(1-phenyl-1H-benzo[d]imidazol-2-yl)-[1,1'-biphenyl]-4-yl)dibenzo[c,h]acridine, (3-(dibenzo[c,h]acridin-7-yl)phenyl)diphenylphosphine oxide (assigned A1 in examples of the present application), (4-(dibenzo[c,h]acridin-7-yl)phenyl)diphenylphosphine oxide (assigned A2 in examples of the present application), 7-(4-(1-phenyl-1H-benzo[d]imidazol-2-yl)phenyl)dibenzo[c,h]acridine.

Suitable hole transport materials (HTM) can be, for instance, HTM from the diamine class, where a conjugated system is provided at least between the two diamine nitrogens. Examples are N4,N4'-di(naphthalen-1-yl)-N4,N4'-diphenyl-[1,1'-biphenyl]-4,4'-diamine (HTM1), N4,N4,N4", N4"-tetra([1,1'-biphenyl]-4-yl)-[1,1':4',1"-terphenyl]-4,4"-diamine (HTM2), N4,N4"-di(naphthalen-1-yl)-N4,N4"-diphenyl-[1,1':4',1"-terphenyl]-4,4"-diamine (HTM3), The synthesis of diamines is well described in literature; many diamine HTMs are readily commercially available.

It will be understood that the aforementioned matrix materials may also be used in a mixture with one another or with other materials in the context of the invention. It will be understood that use may also be made of suitable other organic matrix materials which have semiconductive properties.

In another preferred embodiment, the substantially organic layer is present in a pn junction, the pn junction having at least two layers, namely a p- and n-layer, and optionally an interlayer i in between, wherein the interlayer i and/or the n-layer is (are) the substantially organic semiconducting layer.

The organic electronic device may additionally comprise a polymer semiconducting layer.

Most preferably, the organic electronic device is a solar cell or a light emitting diode.

The organic electronic device may be also a field effect transistor comprising a semiconducting channel, a source electrode, and a drain electrode, the substantially organic layer being provided in between the semiconducting channel and at least one of the source electrode and the drain electrode.

In a further most preferred embodiment, the substantially organic layer comprising the compound bearing at least one lithoxy group and containing at least one heterocyclic ring comprising a phosphine oxide group directly bound to three carbon atoms (preferably a compound according to formula (I)) is an electron injection layer and/or an electron transport layer.

Any layers of the inventive organic electronic device, especially the substantially organic layer can be deposited by known techniques, such as vacuum thermal evaporation (VTE), organic vapour phase deposition, laser induced thermal transfer, spin coating, blade or slit coating, inkjet printing, etc. A preferred method for preparing the organic electronic device according to the invention is vacuum thermal evaporation.

Injection Layer

In a preferred embodiment, the substantially organic layer, having the compound according to formula (I) as its main component, is adjacent to a cathode, preferably between a cathode and one of an ETL (electron transporting layer) or HBL (hole blocking layer). The present invention has the advantages that, especially for non-inverted structures, the simplest form is also the one with a significantly improved performance compared to the structure not using an injection layer. The compound according to formula (I) can be used as a pure layer and is then preferably the only layer between an electron transporting layer (ETL or HBL) and the cathode. In this regard for an OLED the EML and ETL matrix can be the same if the emission zone is far from the cathode. In another embodiment, the ETL and the EML are layers of different composition, preferably of a different matrix.

Such a pure layer as injection layer in organic electronic devices has a preferable thickness between 0.5 nm and 5 nm.

The thickness of the layer comprising the compound according to formula (I) is the nominal thickness, such thickness is usually calculated from the mass deposited on a certain area by the knowledge of the material's density. For example, with vacuum thermal evaporation VTE, the nominal thickness is the value indicated by the thickness monitor equipment. In reality, since the layer is not homogeneous and not flat at least at one interface, its final thickness is difficult to measure, in this case, the average value can be used. The cathode in this regard is a conductive layer having optionally any surface modifications to modify its electrical properties, e.g. to improve its work-function or conductivity. Preferably, the cathode is a double layer, more preferably it is a single layer to avoid complexity.

Semiconducting Layer

It is even preferred that the organic layer is an electron transport layer adjacent to the cathode and comprising the compound according to formula (I). If the ETL is directly adjacent to the cathode, this simplification has the advantage that no additional injection layer is required. Alternatively, an additional injection layer can be provided between the ETL and the cathode. This additional layer can be a layer having the chemical compound according to formula (I) as its main component, as already illustrated above. In one even preferred embodiment, the ETL is beneath the cathode (no other layer in between) wherein the cathode is the top electrode, which is formed after forming the ETL (non-inverted structure).

For an OLED the EML (light emitting layer) and ETL matrix can be the same if the emission zone is far from the cathode. In another embodiment, the ETL and the EML are layers of different composition, preferably of a different matrix.

Polymer Hybrid OLED or Solar Cell in a further preferred embodiment the substantially organic layer comprising the chemical compound according to formula (I) is used in combination with a polymer semiconductor, preferably between a cathode and a polymer layer, wherein the polymer layer preferably comprises the optoelectronic active region of the device (emitting region of an OLED or the absorbing region of a solar cell). All alternatives of layers comprising the chemical compound according to formula (I) or being composed thereof can be used in combination with that polymer layer. Exemplary alternative layers can be an injection layer being composed of the chemical compound according to formula (I), an injection layer comprising the chemical compound and a metal, an electron transport layer having the chemical compound with or without a metal. The electronic interface to the cathode is then strongly improved given the high electron injection capability of the chemical compound (I).

Electrical Doping

The invention can be used as an alternative to conventional redox doping of organic semiconducting layers. By using the term redox doping it is meant specific case of electrical doping using strong oxidizing or reducing agents as explained above. This doping can also be called charge transfer doping. It is known that the redox doping increases the density of charge carriers of a semiconducting matrix towards the charge carrier density of the undoped matrix. An electrically doped semiconductor layer may also have an increased effective mobility in comparison with the undoped semiconductor matrix.

US2008227979 discloses in detail the doping of organic transport materials, also called matrix, with inorganic and with organic dopants. Basically, an effective electronic transfer occurs from the dopant to the matrix increasing the Fermi level of the matrix. For an efficient transfer in a p-doping case, the LUMO energy level of the dopant is preferably more negative than the HOMO energy level of the matrix or at least slightly more positive, not more than 0.5 eV, to the HOMO energy level of the matrix. For the n-doping case, the HOMO energy level of the dopant is preferably more positive than the LUMO energy level of the matrix or at least slightly more negative, not lower than 0.5 eV, to the LUMO energy level of the matrix. It is further more desired that the energy level difference for energy transfer from dopant to matrix is smaller than +0.3 eV.

Typical examples of doped hole transport materials are: copperphthalocyanine (CuPc), which HOMO level is approximately −5.2 eV, doped with tetrafluoro-tetracyano-quinonedimethane (F4TCNQ), which LUMO level is about −5.2 eV; zincphthalocyanine (ZnPc) (HOMO=−5.2 eV) doped with F4TCNQ; a-NPD (N,N'-Bis(naphthalen-1-yl)-N,N'-bis(phenyl)-benzidine) doped with F4TCNQ; a-NPD doped with 2,2'-(perfluoronaphthalene-2,6-diylidene) dimalononitrile (PD1); a-NPD doped with 2,2',2"-(cyclopropane-1,2,3-triylidene)tris(2-(p-cyanotetrafluorophenyl)acetonitrile) (PD2). PD2 was used in the examples of the present application as p-dopant.

One of the preferred modes of the invention is an OLED with the hole transporting side of OLED comprising a p-dopant and the electron transporting side comprising the material according to Formula (I). For example: an OLED with a p-doped HTL and an ETL with a ETM and the material according to Formula (I).

SHORT SUMMARY OF THE FIGURES

ORGANIC ELECTRONIC DEVICES

Figure 1:
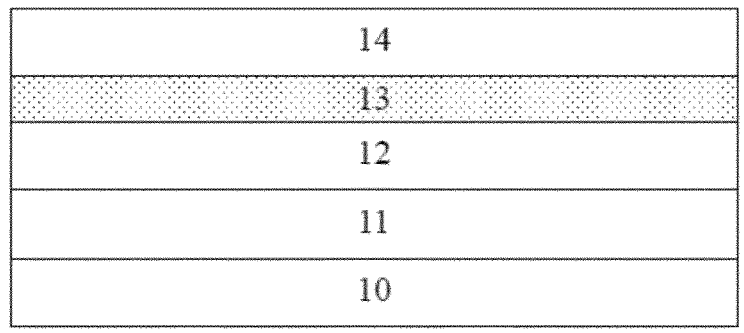
FIG. 1 illustrates a first embodiment of an inventive organic electronic device.

FIG. 1 illustrates a first embodiment of an inventive organic electronic device in the form of a stack of layers forming an OLED or a solar cell. In FIG. 1, 10 is a substrate, 11 is an anode, 12 is an EML or an absorbing layer, 13 is a EIL (electron injection layer), 14 is a cathode.

The layer 13 can be a pure layer of the heterocyclic compound bearing at least one lithoxy group and containing at least one heterocyclic ring comprising a phosphine oxide group directly bound to three carbon atoms, preferably a compound according to formula (I). At least one of the anode and cathode is at least semi-transparent. Inverted structures are also foreseen (not illustrated), wherein the cathode is on the substrate (cathode closer to the substrate than the anode and the order of the layers 11-14 is reversed). The stack may comprise additional layers, such as ETL, HTL, etc.

Figure 2:
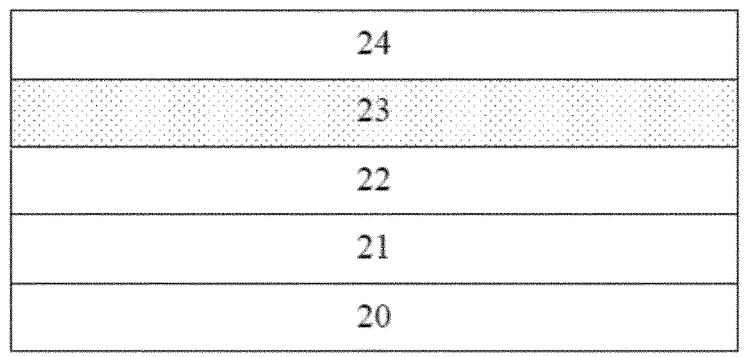
FIG. 2 illustrates a second embodiment of an inventive organic electronic device.

FIG. 2 represents a second embodiment of the inventive organic electronic device in the form of a stack of layers forming an OLED or a solar cell. Here, 20 is a substrate, 21 is an anode, 22 is an EML or an absorbing layer, 23 is an ETL, 24 is a cathode. The layer 23 comprises an electron transport matrix material and a compound according to formula (I).

Figure 3:
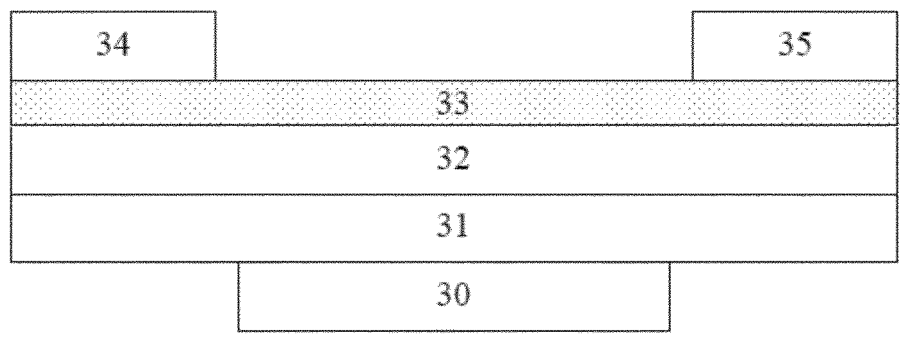
FIG. 3 shows a third embodiment of an inventive organic electronic device.

FIG. 3 illustrates a third embodiment of the inventive device in the form of an OTFT, with semi-conductor layer 32, a source electrode 34 and a drain electrode 35. An unpatterned (unpatterned between the source and drain electrodes) injection layer 33 provides charge carrier injection and extraction between the source-drain electrodes and semi-conducting layer. OTFT also comprises a gate insulator 31 (which could be on the same side as the source drain electrodes) and a gate electrode 30, which gate electrode 30 is on the side of the layer 31 which is not in contact with the layer 32. Obviously, the whole stack could be inverted. A substrate may also be provided. Alternatively, insulator layer 31 may be the substrate.

EXAMPLES

Following compounds were used as electron transporting matrices for testing the effects of inventive compounds:

A1
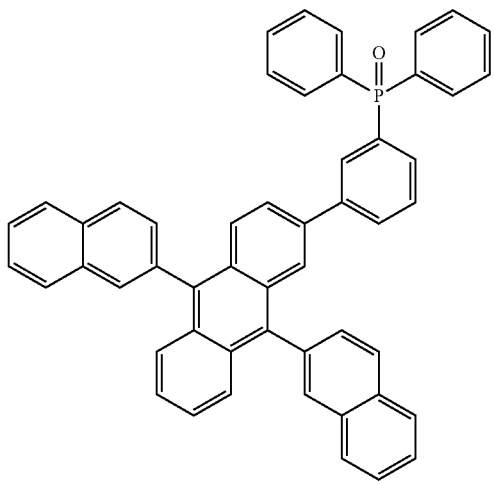

A2
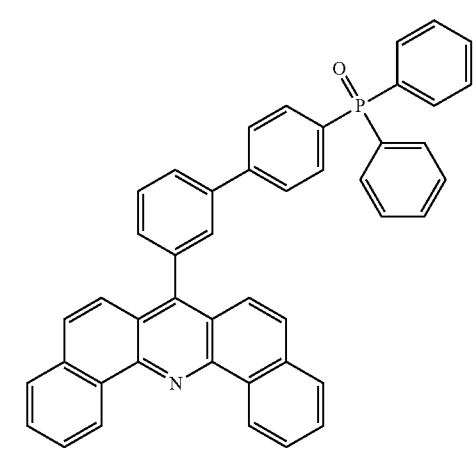

A3
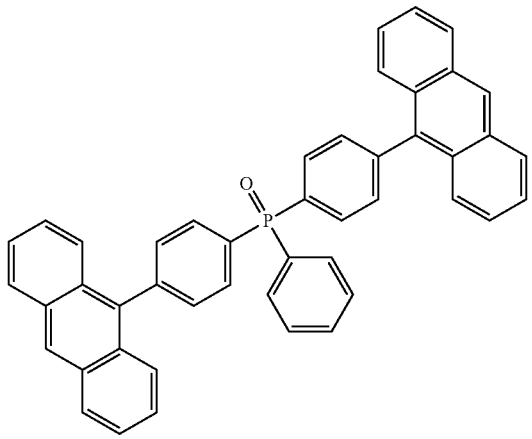

A1 is described in the application EP13187905, A2 was prepared by procedure generally described in the application WO2011/154131, A3 also encompasses the procedures used in EP13187905. Their syntheses are further described in detail.

All reactions were performed under inert atmosphere. Commercial reactants and reagents were used without further purification. Reaction solvents tetrahydrofuran (THF), acetonitrile (AcN) and dichloromethane (DCM) were dried by a solvent purification system (SPS). CV stands throughout this application for cyclic voltammetry, not for curriculum vitae.

Electron Transport Matrix Preparation

General Procedure A: Triphenylphosphinoxide Synthesis

The halogen compound was dissolved in THF. 2.5M n-BuLi solution in hexane was slowly dropped to this solution chilled to −80° C. (temperature measured directly in the solution). The stirring was continued for one hour. Diphenyl phosphine chloride or phenylphosphine dichloride, respectively, was added slowly at −80° C. The reaction mixture was allowed to warm to RT and stirred overnight. After methanol addition and reduction to dryness, the residue was dissolved in DCM. The organic phase was washed with water, dried over $Na_2SO_4$ and reduced to dryness.

The residue was dissolved in DCM again and oxidized with 30 wt. % aqueous hydrogen peroxide solution. After stirring overnight, the organic solution was washed with water, dried over $Na_2SO_4$ and reduced to dryness. The crude product was purified by column chromatography.

General Procedure B: Suzuki Coupling

The halogen compound, the boronic acid, $Pd(P^tBu_3)_4$ and the solvent were mixed together. A degassed 2M aqueous $K_2CO_3$ solution was added. The mixture was stirred at 85° C. (oil bath temperature) for 18 h and cooled afterwards. In case that a solid precipitated, the solid was filtered off and purified by column chromatography directly. Otherwise, the organic phase was washed with water, dried over $Na_2SO_4$, reduced to dryness and purified by column chromatography afterwards.

Precursor Compounds
(3-bromophenyl)diphenylphosphine oxide

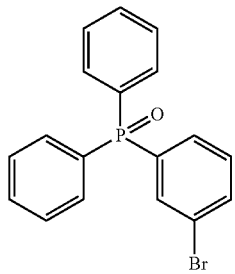 [SMILES: O=P(c1ccccc1)(c1ccccc1)c1cccc(Br)c1]

According to general procedure A
1,3-dibromobenzene: 10.00 g (42.4 mmol, 1.0 eq)
n-butyl lithium, 2.5M in hexane: 17 mL (42.4 mmol, 1.0 eq)
chlorodiphenylphosphine: 9.35 g (42.4 mmol, 1.0 eq)
THF: 50 mL
DCM: 50 mL
$H_2O_2$, 30 wt. % in water: 10 mL
Column chromatography: $SiO_2$, ethyl acetate, $R_f$=0.52
Yield: 9.6 g white solid (63%)
mp: 95° C.
GC-MS: m/z=356, 358

(4-bromophenyl)diphenylphosphine oxide

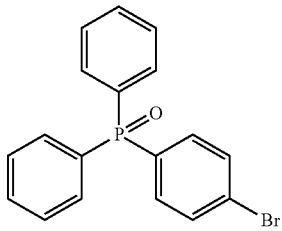 [SMILES: O=P(c1ccccc1)(c1ccccc1)c1ccc(Br)cc1]

According to general procedure A)
1,4-dibromobenzene: 10.00 g (42.4 mmol, 1.0 eq)
n-butyllithium, 2.5M in hexane: 17 mL (42.4 mmol, 1.0 eq)
chlorodiphenylphosphine: 9.35 g (42.4 mmol, 1.0 eq)
THF: 50 mL
DCM: 50 mL
$H_2O_2$, 30 wt. % in water: 10 mL
Column chromatography: $SiO_2$, ethyl acetate
Yield: 6.84 g white solid (45% theoretical)
mp: 166° C.
GC-MS: m/z=356, 358 bis(4-bromophenyl)(phenyl)phosphine oxide

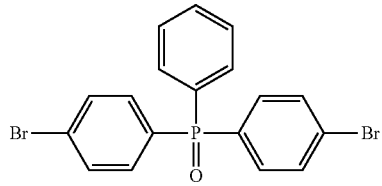 [SMILES: O=P(c1ccccc1)(c1ccc(Br)cc1)c1ccc(Br)cc1]

According to general procedure A
1,4-dibromobenzene: 10.00 g (42.4 mmol, 1.0 eq)
n-butyl lithium, 2.5M in hexane: 17 mL (42.4 mmol, 1.0 eq)
phenyl dichlorophosphine: 3.79 g (21.2 mmol, 0.5 eq), dissolved in 50 mL THF
THF: 100 mL
DCM: 50 mL
$H_2O_2$, 30 wt. % in water: 10 mL
Column chromatography: $SiO_2$, ethyl acetate
Yield: 5.0 g viscous oil (54%)
mp: 125° C.
GC-MS: m/z=433, 435, 437

ETL matrices
(3-(9,10-di(naphthalen-2-yl)anthracen-2-yl)phenyl)diphenylphosphine oxide (A1)
According to general procedure B
(3-bromophenyl)diphenylphosphine oxide: 1.9 g (5.3 mmol, 1.0 eq)
(9,10-di(naphthalen-2-yl)anthracen-2-yl)boronic acid: 3.0 g (6.3 mmol, 1.2 eq)
$Pd(PPh_3)_4$: 183 mg (0.16 mmol, 3 mol. %)
$K_2CO_3$, 2M: 8 mL
DME: 20 mL
Column chromatography: $SiO_2$, ethyl acetate
Yield: 3.1 g (83%) yellow solid
mp: n.a. (glassy)
EI-MS: m/z=706
reduction potential (CV, reversible in THF)-2.38 V.

(3'-(dibenzo[c,h]acridin-7-yl)-[1,1'-biphenyl]-4-yl)diphenylphosphine oxide (A2)
The compound has been prepared from diphenyl(3'-(5,6,8,9-tetrahydrodibenzo[c,h]acridin-7-yl)-[1,1'-biphenyl]-4-yl)phosphine oxide by oxidation with 4,5-dichloro-3,6-dioxocyclohexa-1,4-diene-1,2-dicarbonitrile (DDQ), by a general dehydrogenation procedure described in WO2013/079217. The penultimate intermediate has been prepared by Kumada coupling from (4-bromophenyl)diphenylphosphine oxide described above and 7-(3-bromophenyl)-5,6,8,9-tetrahydrodibenzo[c,h]acridine described as intermediate f (CAS 1352166-94-9) in WO2013/079217.
Melting point 289.7° C. (DSC peak), reduction potential (CV, reversible in THF)-2.25 V.

phenylbis(4-(anthracen-9-yl)phenyl)phosphine oxide (A3)
According to general procedure B
bis(4-bromophenyl)(phenyl)phosphine oxide: 5.0 g (1.0 eq, 11.5 mmol)
anthracen-9-ylboronic acid: 9.33 g (3.66 eq, 41.4 mmol)
tetrakis(triphenylphosphine)palladium (0): 0.529 g (4 mol %, 0.46 mmol)
potassium carbonate 6.33 g (4.0 eq, 45.8 mmol)
1,2-dimethoxyethane 60 mL
Column chromatography: $SiO_2$, ethyl acetate/hexane (volume ratio 1:1), ethyl acetate
Yield: 3.7 g (51%) pale yellow solid
Melting point 294.7° C. (DSC peak), reduction potential (CV, reversible in THF)-2.42 V.

Synthetic Procedure for Preparing the Compounds of Formula (I)

Synthesis Example 1: lithium 2-(5-oxidobenzo[b]phosphindol-5-yl)phenolate (D1)

Step 1: 2,2'-dibrom-1,1'-biphenyl

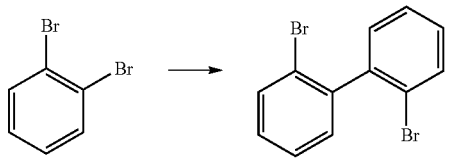 [SMILES: Brc1ccccc1Br ; Brc1ccccc1-c1ccccc1Br]

| 1,2-dibrombenzene | 20 g, 1.0 eq, 84.8 mmol |
| n-butyllithium | 17.0 mL, 0.5 eq, 42.4 mmol |
| THF | 150 mL |

Starting compounds were dissolved in dry THF and the 2.5 M butyllithium solution in hexanes had been added very slowly at −78° C. The reaction mixture was kept at this temperature for 1 h, then the temperature was allowed to reach the room temperature (RT). After further 3 h stirring, 80 mL water were added and the formed immiscible layers allowed to separate. The organic phase was then washed 3 times with 80 mL water to remove residual lithium salt by-products, dried over anhydrous magnesium sulphate and evaporated under reduced pressure, to afford a brown oil that under dissolution in hot ethanol and cooling crystallized as a white solid.

Yield: 9.7 g (73%), white powder $^1$H-NMR (CDCl$_3$, 300 MHz): δ (ppm) 7.97 (dd, J=8 Hz and 1 Hz, 2H), 7.44 (ddd, J=7.6 Hz, 7.6 Hz and 1 Hz, 2H), 7.22 (dd, J=7.6 Hz and 1.5 Hz, 2H), 7.11 (ddd, J=8 Hz, 7.6 Hz and 1.5 Hz, 2H).

Step 2: 5-phenyl-5H-benzo[b]phosphindole-5-oxide

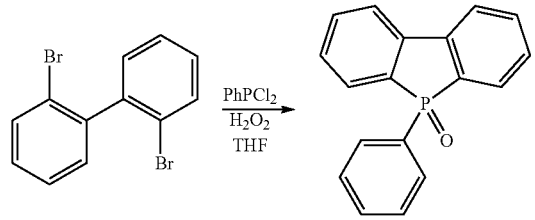 [SMILES: "PhPCl2" ; Brc1ccccc1-c1ccccc1Br ; O=P1(c2ccccc2)c2ccccc2-c2ccccc21 ; "H2O2THF"]

| 2,2'-dibrom-1,1'-biphenyl | 9.7 g, 1.0 eq., 31.0 mmol |
| phenylphosphine dichloride | 5.5 mL, 1.3 eq., 40.0 mmol |
| THF | 100 mL |
| n-butyl lithium (n-BuLi) | 25.0 mL, 2.0 eq., 62.5 mmol |
| Hydrogen peroxide | 20 mL, excess |

2,2'-dibrom-1,1'-biphenyl was dissolved in dry THF and cooled to −78° C. 2.5M n-BuLi solution in hexanes was added dropwise under stirring to the reaction mixture at this temperature and the mixture was further stirred for 2 h. Then, phenyl dichlorophosphine was added at −78° C. dropwise, the temperature was allowed to rise slowly to room temperature and the reaction mixture left stirring at RT overnight. Hydrogen peroxide (aqueous solution, 27 wt. %) was added slowly at RT and the mixture was stirred at RT for 1 h. The mixture was diluted with water and extracted with ethyl acetate. The organic phase was dried over magnesium sulphate and the solvent removed under reduced pressure. The obtained colorless oil was dissolved in ethyl acetate and purified by column chromatography on silica with ethyl acetate/n-heptane mixture (1:1 volume ratio) as eluent (R$_f$=0.2).

Yield: 6.0 g (75%), white powder $^1$H-NMR (CD$_2$Cl$_2$, 300 MHz): δ (ppm)=7.88 (m, 2H), 7.72-7.57 (m, 6H), 7.51 (m, 1H), 7.44-7.36 (m, 4H). $^{31}$P-NMR (CD$_2$Cl$_2$, 121 MHz): δ (ppm)=32.0 (s)

Step 3: 5-(2-hydroxyphenyl)-5H-benzo[b]phosphindole-5-oxide

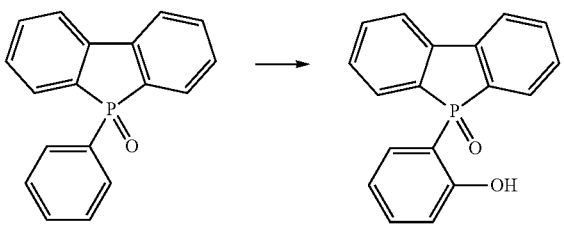 [SMILES: O=P1(c2ccccc2)c2ccccc2-c2ccccc21 ; O=P1(c2ccccc2O)c2ccccc2-c2ccccc21]

| 5-phenyl-5H-benzo[b]phosphindole-5-oxide | 21.07 g, 1.0 eq., 103.4 mmol |
| lithium diisopropylamide (LDA) | 14 mL, 2.0 eq., 20.8 mmol |
| 2-isopropoxy-4,4,5,5-tetramethyl-1,3,2-dioxaborolane | 6.3 mL, 3.0 eq., 31.2 mmol |
| THF | 60 mL |
| chloroform | 60 mL |
| hydrogen peroxide | 20 mL |

5-phenyl-5H-benzo[b]phosphindole-5-oxide was dissolved in dry THF and cooled to −78° C. 2-isopropoxy-4,4,5,5-tetramethyl-1,3,2-dioxaborolane was added at the same temperature and after 20 minute stirring, the 1.5M LDA solution in cyclohexane was added dropwise under stirring, the reaction mixture was allowed to warm to RT and further stirred for 24 h. The solvent was removed under reduced pressure and the residue dissolved in chloroform. Hydrogen peroxide (aqueous solution, 27 wt. %) was added slowly at 0° C. and the mixture was stirred at RT overnight. After chloroform extraction and washing the organic phase with brine, drying over magnesium sulphate and evaporation under reduced pressure, the residue was dissolved in DCM and precipitated with pentane. The purified solid was filtered off, washed with pentane and dried in vacuum.

Yield: 1.9 g (63%), white powder $^1$H-NMR (CDCl$_3$, 300 MHz): δ (ppm)=11.17 (s, 1H, —OH), 7.87-7.76 (m, 4H), 7.47-7.32 (m, 3H), 7.01 (ddd, J=5.09 Hz, 8.48 Hz and 0.75 Hz, 1H, OH$_{ortho}$), 6.64 (m, 1H), 6.52 (ddd, J=7.72 Hz, 1.70 Hz and 15.45 Hz, 1H).

$^{31}$P-NMR (CDCl$_3$, 121 MHz): δ (ppm)=46.4 (s)

Step 4: lithium 2-(5-oxidobenzo[b]phosphindol-5-yl)phenolate (D1)

| 5-(2-hydroxyphenyl)-5H-benzo[b]phosphindole-5-oxide | 3.1 g, 1.0 eq., 10.5 mmol |
| lithium tert-butoxide | 0.84 g, 1.0 eq., 10.5 mmol |
| acetonitrile | 120 mL |

The starting material was suspended in dry acetonitrile. Lithium tert-butoxide was added at room temperature and the mixture was heated at reflux for 13 hours. The solid was filtered off, washed with acetonitrile and dried in vacuum. Further purification was made by Soxhlet extraction with dry ethanol/acetonitrile mixture (1:1 volume ratio).

Yield: 2.5 g (80%)

Device Examples

Lithium 2-(diphenylphosphoryl)phenolate (C2), described in an earlier application PCT/EP/2012/074127, and the well-known lithium 8-hydroxyquinolinolate (LiQ, C3) were used as comparative electrical n-dopants; lithium 2-(5-oxidobenzo[b]phosphindol-5-yl)phenolate was used as inventive n-dopant.

Device Example 1

A blue emitting device was made on a commercially available glass substrate with deposited indium tin oxide (ITO) 90 nm thick layer as an anode. A 10 nm layer of HTM3 doped with 2,2',2''-(cyclopropane-1,2,3-triylidene)tris(2-(p-cyanotetrafluorophenyl)acetonitrile) (PD2) (matrix to dopant weight ratio of 92:8) was subsequently deposited as hole injection and transport layer, followed by a 120 nm undoped layer of HTM3. Subsequently, a blue fluorescent emitting layer of ABH113 (Sun Fine Chemicals) doped with NUBD370 (Sun Fine Chemicals) as an emitter (matrix dopant ratio of 97:3 wt. %) was deposited with a thickness of 20 nm. A 36 nm thick ETL having a composition given in the Table 1 was deposited on the emitting layer. A 1 nm thick layer of lithium quinolate (LiQ) followed the ETL, followed by 100 nm thick aluminium layer as a cathode.

The results are shown in the Table 1.

TABLE 1

| ETL | Voltage at 10 mA/cm$^2$ [V] | Quantum efficiency at 10 mA/cm$^2$ [%] | LT$_{97}$ [h] |
| --- | --- | --- | --- |
| A1:D1 (50:50 wt. %) | 4.4 | 5.9 | 44 |
| A1:C2 (50:50 wt. %) | 4.0 | 6.5 | 42 |
| A1:C3 (50:50 wt. %) | 4.2 | 5.6 | 39 |
| A2:D1 (50:50 wt. %) | 4.7 | 6.3 | 66 |
| A2:C2 (50:50 wt. %) | 4.4 | 7.0 | 49 |
| A2:C3 (50:50 wt. %) | 4.6 | 5.5 | 250 |
| A3:D1 (50:50 wt. %) | 5.0 | 4.6 | 300 |
| A3:C2 (50:50 wt. %) | 4.5 | 5.5 | 140 |
| A3:C3 (50:50 wt. %) | 5.0 | 4.0 | 19 |

LT97 stands for the timespan within the luminance of the device operated at given current density had not changed more than 3% of its initial value. "Voltage rise" is another important operational characteristic of OLEDs. In stable devices operated at constant current, the voltage remains constant. Should the voltage in a testing device raise more than 5% of its initial value during the desired lifetime, it is a sign that the tested material makes the device instable.

Advantages of the Invention

Experimental results listed in Table 1 show that performance of inventive OLEDs is fully comparable with OLEDs using state-of-the-art ETM additives C2 and C3. Inventive heterocyclic compounds bearing at least one lithoxy group and containing at least one heterocyclic ring comprising a phosphine oxide group directly bound to three carbon atoms thus significantly broaden the offer of additives for improving electron transport and/or electron injection in organic electronic devices and allow further improving and optimizing performance of organic electronic devices beyond limits known in the art.

Moreover, it was surprisingly found that the presence of the phosphine oxide group in a ring structure increases thermal stability of the additive in comparison with similar structures lacking the ring.

Thus, C2 has an onset of the decomposition peak estimated from TGA-DSC measurement at the temperature 432° C. and decomposition peak at 442° C., whereas its cyclic analog D1 showed decomposition onset at 484° C. and decomposition peak 495° C.

It was further found that in couples of compounds with comparable molecular weight and structure, like C2 and D1, the compound wherein the phosphine oxide group is a part of a ring has lower evaporation temperature in high vacuum than the compound with acyclic phosphine oxide group. As a result, electron transport additives according this invention offer, in comparison with conventional phosphine oxide additives, significantly broader processing window in vacuum thermal evaporation, representing significant advantage in contemporary manufacturing processes used for mass production of organic electronic devices.

The features disclosed in the foregoing description, the claims and in the drawings may both separately and in any combination thereof, be material for realising the invention in diverse forms thereof.

ABBREVIATIONS USED THROUGHOUT THE APPLICATION

Alq3 aluminium tris(8-hydroxyquinolinolate)
BPhen bathophenanthroline
CV cyclic voltammetry
DCM dichloromethane
EML (light) emitting layer
eq. equivalent
ETL electron transport layer
ETM electron transport material
GCMS gas chromatography (combined with) mass spectroscopy
$^1$H-NMR proton magnetic resonance
HBL hole blocking layer
HIL hole injecting layer
HOMO highest occupied molecular orbital
HTL hole transport layer
LiQ lithium 8-hydroxyquinolinolate
LUMO lowest unoccupied molecular orbital
mol, molar (e.g. percent)
OLED organic light emitting device
OTFT organic thin film transistor
HPLC-MS high performance liquid chromatography-mass spectroscopy
THF tetrahydrofuran
TGA-DSC thermogravimetric analysis—differential scanning calorimetry
TCO transparent conductive oxide
VTE vacuum thermal evaporation
wt. % weight percent

The invention claimed is:

1. Organic electronic device, comprising a first electrode, a second electrode, and, between the first and the second electrode, a substantially organic layer comprising a heterocyclic compound bearing at least one lithoxy group and containing at least one heterocyclic ring comprising a phosphine oxide group directly bound to three carbon atoms.

2. Organic electronic device according to claim 1, wherein the lithoxy group is directly attached to an aromatic or heteroaromatic structural moiety.

3. Organic electronic device according to claim 1, wherein the heterocyclic ring comprising the phosphine oxide group is a five-, six- or seven-membered ring.

4. Organic electronic device according to claim 1, wherein the heterocyclic compound bearing at least one lithoxy group and containing at least one heterocyclic ring comprising a phosphine oxide group directly bound to three carbon atoms has formula (I):

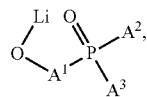

formula (I)

wherein $A^1$ is a $C_6$-$C_{30}$ arylene or $C_2$-$C_{30}$ heteroarylene, each of $A^2$ and $A^3$ is independently selected from a $C_6$-$C_{30}$ aryl and $C_2$-$C_{30}$ heteroaryl, and $A^2$ with $A^3$ are linked to each other.

5. Organic electronic device according to claim 1, wherein the substantially organic layer comprises an electron transport matrix compound.

6. Organic electronic device according to claim 5, wherein the electron transport matrix compound comprises an imidazole or a P=O functional group.

7. Organic electronic device according to claim 5, wherein the heterocyclic compound and the electron transport matrix compound are present in the substantially organic layer in the form of a homogeneous mixture.

8. Organic electronic device according to claim 1, wherein the device is an organic light emitting diode, an organic solar cell, or an organic field effect transistor.

9. Organic electronic device according to claim 8, wherein the device is the organic light emitting diode with the first electrode being an anode, the second electrode being a cathode, and the device further comprising a light emitting layer between the anode and the cathode and wherein the substantially organic layer is arranged between the cathode and the light emitting layer.

10. Heterocyclic compound bearing at least one lithoxy group and containing at least one heterocyclic ring comprising a phosphine oxide group directly bound to three carbon atoms has formula (I)

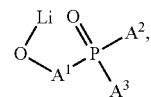

formula (I)

wherein $A^1$ is a $C_6$-$C_{30}$ arylene or $C_2$-$C_{30}$ heteroarylene, each of $A^2$ and $A^3$ is independently selected from a $C_6$-$C_{30}$ aryl and $C_2$-$C_{30}$ heteroaryl, and $A^2$ with $A^3$ are linked to each other.

11. Compound according to claim 10, wherein $A^1$ is $C_6$-$C_{12}$ arylene or $C_2$-$C_{12}$ heteroarylene.

12. Compound according to claim 10, wherein each of $A^2$ and $A^3$ is independently selected from a $C_6$-$C_{10}$ arylene or $C_2$-$C_{12}$ heteroarylene.

13. Compound according to claim 10, wherein $A^1$ is selected from phenylene and pyridyl-diyl.

14. Compound according to claim 10, wherein $A^1$, $A^2$ and $A^3$ are o-phenylene.

15. Compound having formula (Ia)

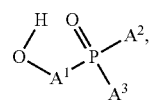

formula (Ia)

wherein $A^1$ is a $C_6$-$C_{30}$ arylene or $C_2$-$C_{30}$ heteroarylene, each of $A^2$ and $A^3$ is independently selected from a $C_6$-$C_{30}$ aryl and $C_2$-$C_{30}$ heteroaryl, and $A^2$ with $A^3$ are linked to each other, as a penultimate precursor for compound of claim 10 having formula (I).

16. Electrically doped semiconducting material comprising at least one electron transport matrix compound and at least one heterocyclic compound bearing at least one lithoxy group and containing at least one heterocyclic ring comprising a phosphine oxide group directly bound to three carbon atoms.

* * * * *